(12) United States Patent
Calignano et al.

(10) Patent No.: US 9,522,192 B2
(45) Date of Patent: Dec. 20, 2016

(54) POLYETHYLENE GLYCOL DERIVATIVES OF PALMITOYLETHANOLAMIDE AND ANALOGOUS ACYLETHANOLAMIDES

(71) Applicant: EPITECH GROUP S.r.l., Milan (IT)

(72) Inventors: Antonio Calignano, Milan (IT); Giuseppe D'Agostino, Milan (IT); Sonia Laneri, Milan (IT); Rosaria Meli, Milan (IT); Carmine Ostacolo, Milan (IT); Roberto Russo, Milan (IT); Antonia Sacchi, Milan (IT); Diana Tronino, Milan (IT); Francesco Della Valle, Milan (IT); Maria Federica Della Valle, Milan (IT); Gabriele Marcolongo, Milan (IT)

(73) Assignee: EPITECH GROUP S.r.l., Milan (IT)

(*) Notice: Subject to any disclaimer, the term of this patent is extended or adjusted under 35 U.S.C. 154(b) by 0 days.

(21) Appl. No.: 14/103,463

(22) Filed: Dec. 11, 2013

(65) Prior Publication Data

US 2015/0157733 A1    Jun. 11, 2015

(30) Foreign Application Priority Data

Dec. 13, 2012  (IT) .............. MI2012A2127

(51) Int. Cl.
| | |
|---|---|
| *A61K 31/164* | (2006.01) |
| *C07C 235/08* | (2006.01) |
| *A61K 47/48* | (2006.01) |
| *C07C 231/12* | (2006.01) |
| *C07C 235/20* | (2006.01) |
| *C08G 59/00* | (2006.01) |

(52) U.S. Cl.
CPC ....... *A61K 47/48215* (2013.01); *A61K 31/164* (2013.01); *C07C 231/12* (2013.01); *C07C 235/08* (2013.01); *C07C 235/20* (2013.01); *C08G 59/00* (2013.01)

(58) Field of Classification Search
CPC ............... C07C 233/20; A61K 47/48215
USPC .......................... 525/54.1; 554/66
See application file for complete search history.

(56) References Cited

U.S. PATENT DOCUMENTS

| 3,821,023 A | 6/1974 | Amati et al. |
| 6,864,285 B1 | 3/2005 | Comelli et al. |

OTHER PUBLICATIONS

Schafer et al. Drug Discovery Today, 2008, 13 21-22, 913-916).*
Horig et al. Journal of Translational Medicine 2004, 2, 44.*
Italian Search Report for corresponding Italian Patent Application No. MI2012A002127 mailed Aug. 26, 2013.
Lambert, D. et al. "Analogues and homologues of N-palmitoylethanolamide, a putative endogenous CB2 cannabinoid, as potential ligands for the cannabinoid receptors", Biochimica et Biophysica ACTA—Molecular and Cell Biology of Lipids, vol. 1440, No. 2-3, Sep. 22, 1999, pp. 266-274.
Bhadra, D. et al. "Pegnology: A review of Pegylated Systems", Die Pharmazie, Govi Verlag Pharmazeutischer Verlag GmbH, Eschborn, Germany, vol. 57, No. 1, Jan. 1, 2002, pp. 5-29.

* cited by examiner

*Primary Examiner* — Yong Chu
*Assistant Examiner* — Ana Z Muresan
(74) *Attorney, Agent, or Firm* — Merchant & Gould P.C.

(57) ABSTRACT

The synthesis of a series of Polyethylene glycol conjugates (esters and carbonates) of PEA and its analogous acylethanolamides, have higher water solubility and good hydrophilic/lipophilic balance, resulting in (i) improved accumulation in tissues (particularly skin and mucosae), (ii) prolonged release, and (iii) increased bioavailability. Improvement of PEA and analogous acylethanolamides levels in the tissues—particularly in the skin and mucosae—and their prolonged release is due to the improved bioavailability of related conjugates. Conjugates are able to extend the time frame in which PEA and analogous acylethanolamides exert their pharmacological effects.

8 Claims, 5 Drawing Sheets

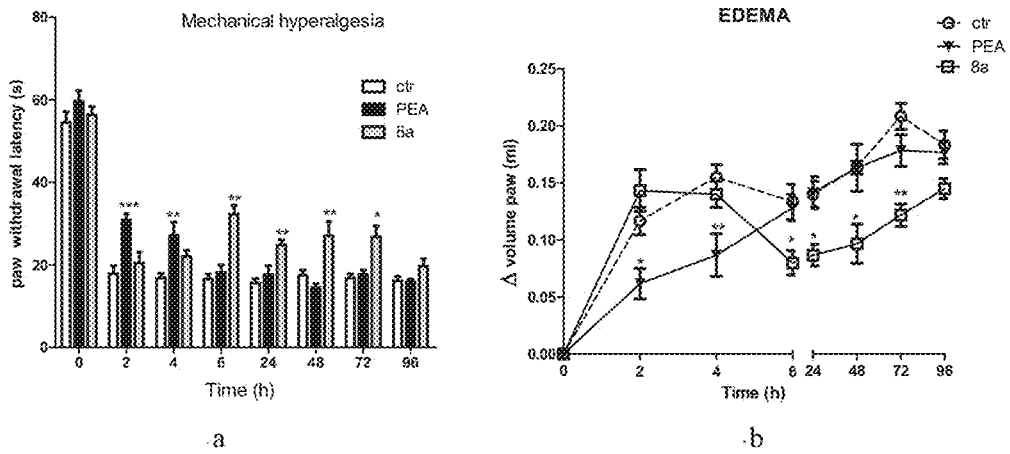
Figure 1: Effect of local application of vehicle (CTR), PEA and derivative 8a on mechanical hyperalgesia (a) and paw oedema (b). Data represent mean ± SEM of 6 mice. *$p<0.05$, $p<0.01$ and *$p<0.001$ vs CTR
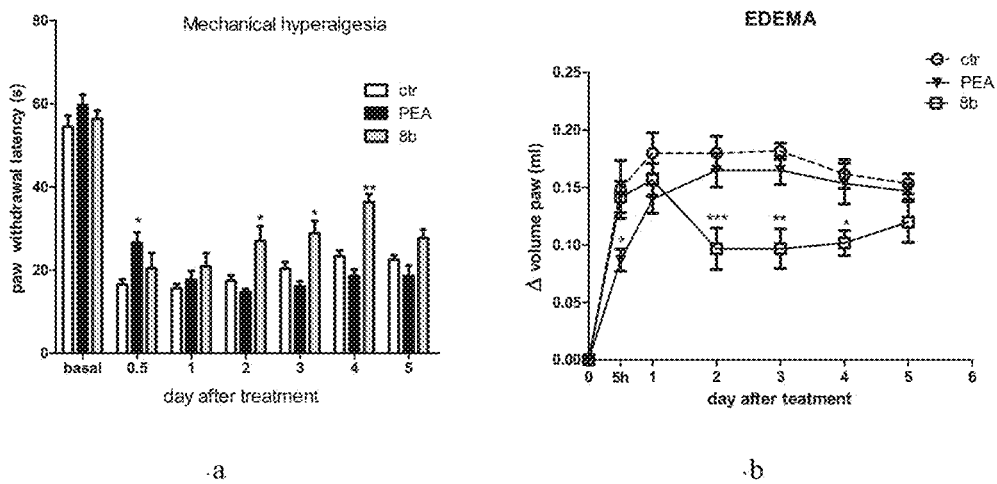
Figure 2: Effect of local application of vehicle (CTR), PEA and derivative 8b on mechanical hyperalgesia (a) and paw oedema (b). Data represent mean ± SEM of 6 mice. *$p<0.05$, $p<0.01$ and *$p<0.001$ vs CTR

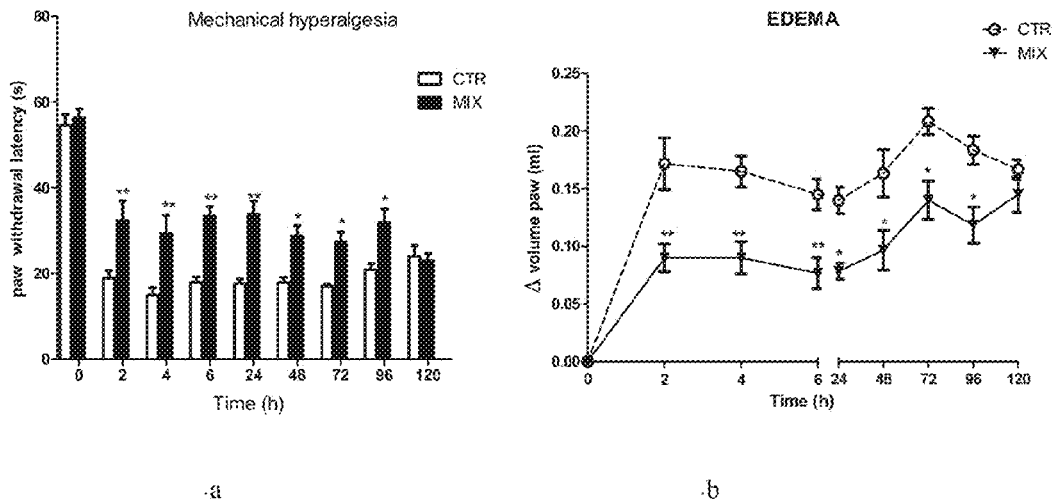
Figure 3: Effect of local application of vehicle (CTR) and PEA+ 8a+8b (MIX) on mechanical hyperalgesia (a) and paw oedema (b). Data represent mean ± SEM of 6 mice. *p<0.05, **p<0.01 and vs CTR
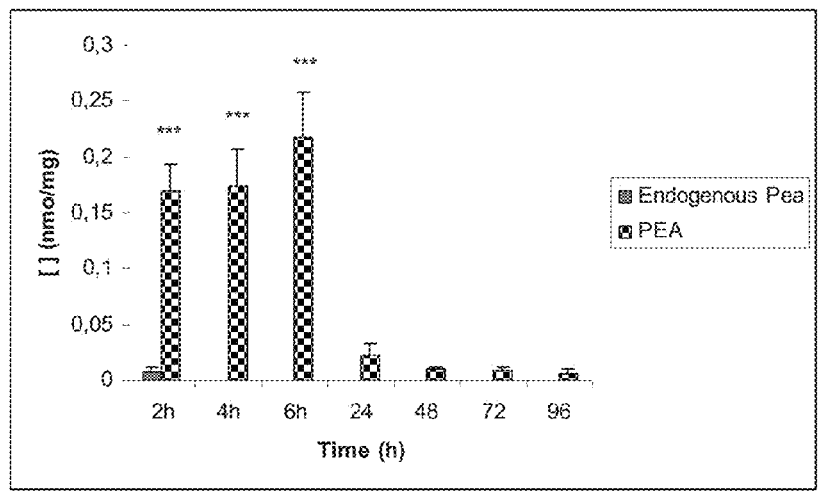
Figure 4: Skin accumulation of PEA

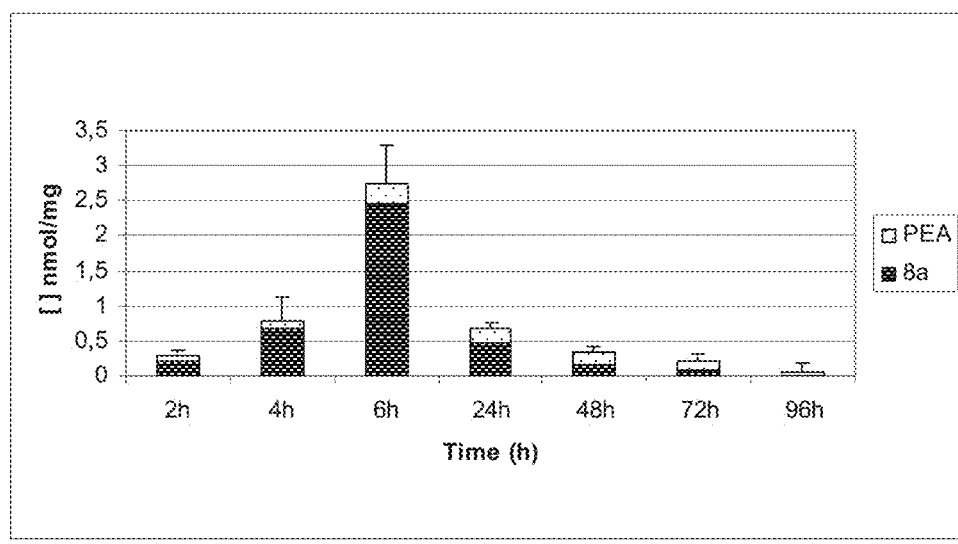
Figure 5: Skin accumulation of derivative 8a

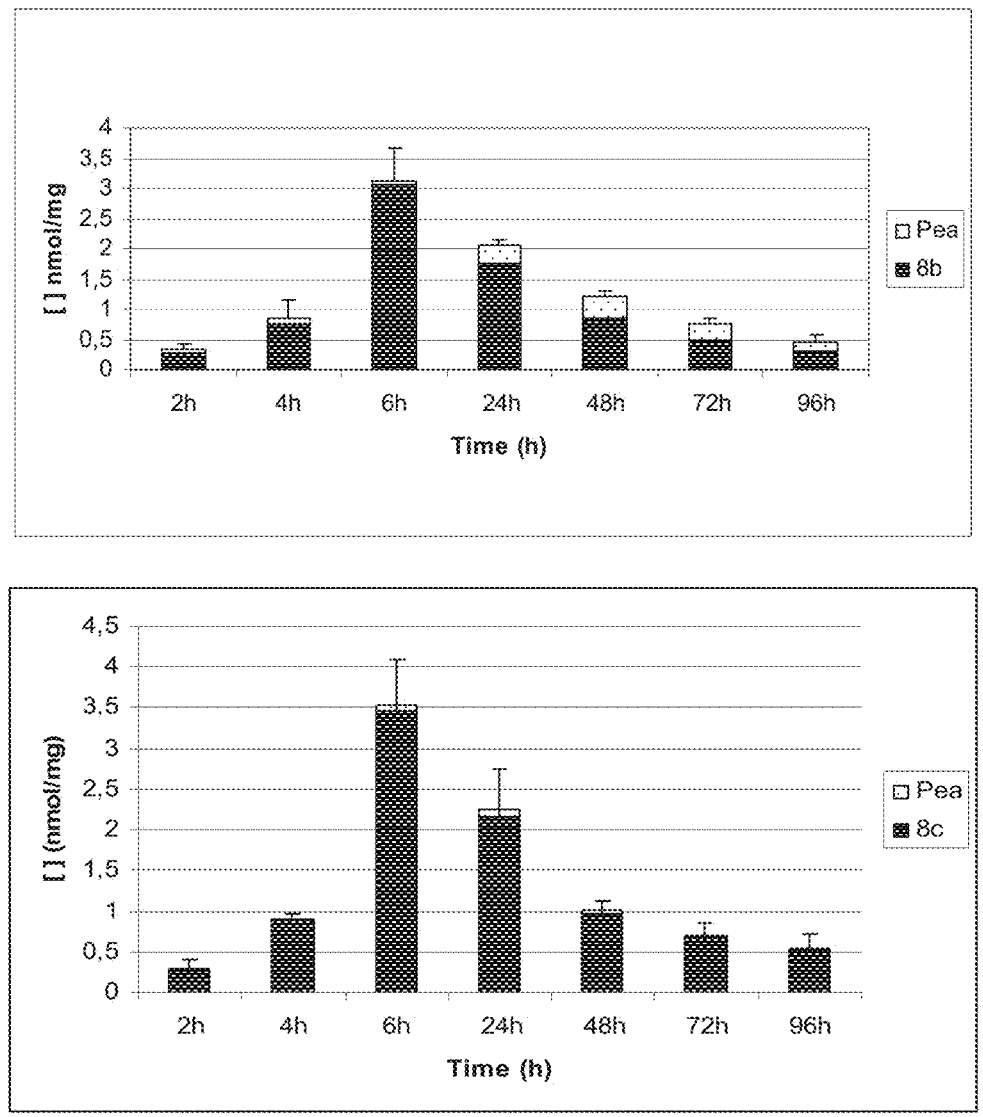
Figure 6: Skin accumulation of derivative 8b and 8c.

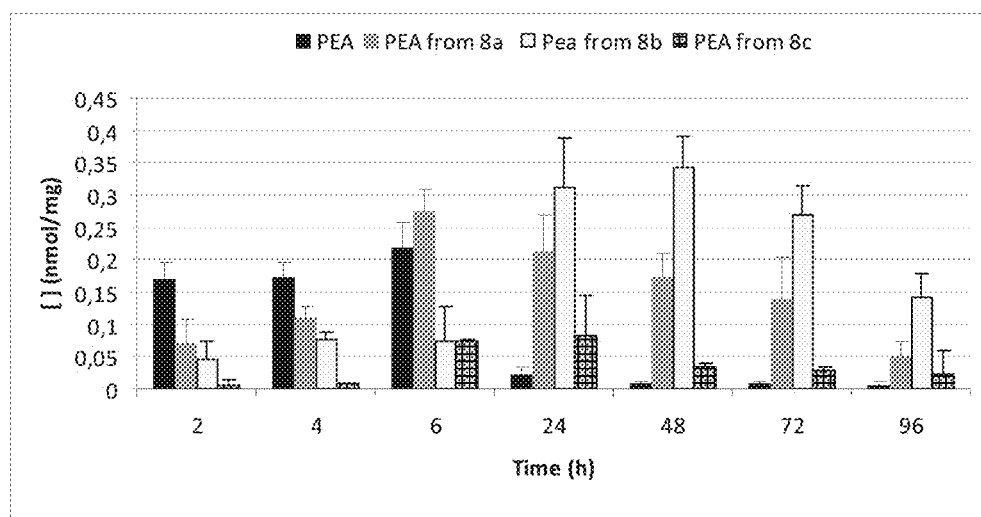
Figure 7: PEA release from synthesized derivatives, compared to the accumulation of the parent drug.

POLYETHYLENE GLYCOL DERIVATIVES OF PALMITOYLETHANOLAMIDE AND ANALOGOUS ACYLETHANOLAMIDES

This application claims benefit of Serial No. MI2012A002127, filed 13 Dec. 2012 in Italy and which application is incorporated herein by reference. To the extent appropriate, a claim of priority is made to each of the above disclosed applications.

FIELD OF THE INVENTION

The present invention relates to polyethylene glycol derivatives of palmitoylethanolamide (PEA) and analogous acylethanolamides, both for topical and systemic administration, having improved physico-chemical properties for the treatment of inflammatory and itch- or pain-associated disorders.

BACKGROUND ART

Palmitoylethanolamide (PEA), the amide of palmitic acid and ethanolamine, is one of the most investigated molecules belonging to the acylethanolamide family. Its analgesic and anti-inflammatory effects have been widely investigated, and mainly depend on the expression of specific membrane or nuclear receptors like Peroxisome Proliferator-Activated Receptor α (PPAR-α), Cannabinoid Receptors (CB), G Protein-coupled Receptor (GPR55), Transient Receptor Potential Cation Channel Subfamily V member 1 (TRPV1).

SUMMARY OF THE INVENTION

The aim of the present invention was to improve the pharmacokinetic and solubility profile of PEA and analogous acylethanolamides both for topical and systemic administration resulting in a longer lasting efficacy.

The present inventors have found that this goal can be achieved by increasing the membrane permeability and solubility of PEA and analogous acylethanolamides by means of the formation of polyethylene glycols conjugates.

It has been found that advantageous effects can be achieved when the conjugates are polyethylene glycol derivatives of PEA or analogous acylethanolamides.

An object of the invention thus are polyethylene glycol derivatives of acylethanolamides of formula (I):

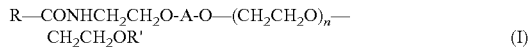
(I)

wherein R—CONHCH$_2$CH$_2$O— is the residue of an acylethanolamide and more in detail,
R is: a linear or branched alkyl chain including from 9 to carbon atoms and preferentially from 15 to 17 carbon atoms or a linear or branched alkenyl chain including from to 21 carbon atoms and preferentially from 15 to 17 carbon atoms and one double bond;
R' is H or a linear or branched alkyl group chosen among methyl-, ethyl-, n-propyl- and isopropyl-;
A is a linker group selected from a dicarboxylic acid residue and a carbonyl group —CO—;
and n is an integer from 1 to 1000.

When A is a dicarboxylic acid residue, it can be selected from succinic, glutaric, maleic and phtalic acid residue.
Another object of the invention is the use of the above derivatives for human or veterinary application.
A further object of the invention is the use of the above derivatives for the treatment of inflammatory diseases (peripheral neurogenic and/or neuroimmunogenic inflammation, central neuroinflammation) by topical or systemic administration (enteric or parenteral administration).

Another more specific object of the invention is the use of the above derivatives for the treatment of skin, mucosal and eye diseases.

Pharmaceutical formulations, containing one or more derivatives of formula (I), together with pharmaceutically acceptable excipients and/or carriers, optionally together with PEA or/and analogous acylethanolamides, is an additional object of the invention.

The invention also relates to a process for synthesizing the derivatives of formula (I).

BRIEF DESCRIPTION OF THE DRAWINGS

FIG. 1: Effect of local application of vehicle (CTR), PEA and derivative 8a on mechanical hyperalgesia (a) and paw oedema (b). Data represent mean±SEM of 6 mice. *$p<0.05$, $p<0.01$ and *$p<0.001$ vs CT;

FIG. 2: Effect of local application of vehicle (CTR), PEA and derivative 8b on mechanical hyperalgesia (a) and paw oedema (b). Data represent mean±SEM of 6 mice. *$p<0.05$, $p<0.01$ and *$p<0.001$ vs CTR;

FIG. 3: Effect of local application of vehicle (CTR) and PEA+ 8a+8b (MIX) on mechanical hyperalgesia (a) and paw oedema (b). Data represent mean±SEM of 6 mice. *$p<0.05$, **$p<0.01$ and vs CTR;

FIG. 4: Skin accumulation of PEA;
FIG. 5: Skin accumulation of derivative 8a;
FIG. 6: Skin accumulation of derivative 8b and 8c;
FIG. 7: PEA release from synthesized derivatives, compared to the accumulation of the parent drug.

DETAILED DESCRIPTION OF THE INVENTION

A first object of the present invention are polyethylene glycol derivatives of acylethanolamides of formula (I):

(I)

wherein R—CONHCH$_2$CH$_2$O— is the residue of an acylethanolamide and more in detail, R is: a linear or branched alkyl chain including from 9 to 21 carbon atoms and preferentially from 15 to 17 carbon atoms or a linear or branched alkenyl chain including from 9 to 21 carbon atoms and preferentially from 15 to 17 carbon atoms and one double bond;
R' is H or a linear or branched alkyl group chosen among methyl-, ethyl-, n-propyl- and isopropyl-;
A is a linker group selected from a dicarboxylic acid residue and a carbonyl group —CO—;
and n is an integer from 1 to 1000.

In an embodiment, n is an integer from 1 to 10. In a particular embodiment, n is an integer from 1 to 3.

According to a different embodiment, n is an integer from 11 up to 1000, particularly from 20 to 200.

In an embodiment, when A is a dicarboxylic acid residue, it can be selected from a succinic, glutaric, maleic and phtalic acid residue.

The compounds of formula (I) can be synthesized by means of a process that includes the following steps:
(a) reaction of an acylethanolamide with a precursor of the linker group A;
(b) reaction of the product of step (a) with a polyethylene glycol of formula HO—(CH$_2$CH$_2$O)$_n$—CH$_2$CH$_2$OR', wherein n is an integer from 1 to 1000 and R' is H or a linear or branched alkyl group chosen among methyl-, ethyl-, n-propyl- and isopropyl-.

When A is the residue of a dicarboxilic acid, its precursor is the corresponding anhydride.

Step (b) can be performed in the presence of suitable condensing agents, like a carbodiimide and preferably dicyclohexylcarbodiimide.

In another embodiment, the free carboxylic group of the intermediate produced in step (a) can be activated by the formation of a chloride, bromide or iodide derivative or with suitable leaving groups (e.g. alkyloxycarbonyloxy-, succinimidyloxy), and the condensation reaction can then be performed in the presence or absence of a catalyst.

In another embodiment, the polyethylene glycol, optionally end-capped with a group R' corresponding to a linear or branched alkyl group chosen among methyl-, ethyl-, n-propyl- and isopropyl-, could be activated by replacement of the terminal hydroxyl group with a good leaving group, like methanesulfonate, p-toluenesulfonate or trifluoromethanesulfonate. Free carboxylic group of the intermediate produced in step (a) can be reacted with the activated polyethylenglycol in the presence or absence of a base or a catalyst.

In another embodiment, when A is a —CO— residue, the precursor of the linker A is for example a chlorocarbonyl-residue, obtained by a safe and useful substitute for phosgene like triphosgene, or an imidazolecarbonyl-residue obtained by carbonyldiimidazole. The conjugation of the Acylethanolamide with PEG "via" C=O carbonyl linker can be obtained either introducing the active chlorocarbonyl- or imidazolecarbonyl- onto the acylethanolamide and then reacting with the PEG, or introducing the active chlorocarbonyl or imidazolecarbonyl onto the alkoxy-PEG and then reacting with the acylethanolamide.

Acylethanolamides can be synthesized according to well know prior art methods, such as the one described in N Ueda, K Yamanaka, Y Terasawa, S Yamamoto "An acid amidase hydrolyzing anandamide as an endogenous ligand for cannabinoid receptors" FEBS Lett 454:267-270 (1999), which describes the reaction of palmitic acid with 2-ethanolamine.

Experimental Part
Synthesis and Characterizations of Acylethanolamides Conjugates $^1$H and $^{13}$C NMR were recorded using a Mercury plus 400 MHz instrument (Varian Inc., Palo Alto, Calif., USA), using trimethylsilane (TMS) as internal standard. Chemical shifts values are reported in δ units (ppm) relative to TMS (1%). The mass spectra were recorded using an API 2000 instrument equipped with a Data system software analyst 1.3 (Applied Byosystem, Foster City, USA).

Example 1

Palmitoylethanolamide Hemisuccinate (Intermediate 1)

1.00 g of PEA (3.36 mmol) was mixed with 0.44 g of Succinic anhydride (4.36 mmol), in 30 ml of anhydrous Dimethylformamide. The mixture was stirred at room temperature for 18 h. Then a 2N HCl solution was added and the aqueous phase was extracted 3 times with chloroform. The organic layers were collected, dried over anhydrous MgSO$_4$ and evaporated in vacuum. The crude product was purified by chromatography on a silica gel column using 9.5/0.5 chloroform/methanol as eluent. The course of reaction and purification was monitored by TLC on silica gel plates, eluted with 9.5/0.5 chloroform/methanol and developed by oxidation with permanganate stain. Yield: 83%.

$^1$H NMR (CDCl$_3$): d 0.88 (t, 3H, J=6.8, CH$_3$), 1.22-1.40 (m, 26H, CH$_2$), 1.60-1.65 (m, 2H, CH$_2$), 2.20 (t, 2H, J=70.5, CH$_2$CO), 2.65 (t, 2H, J=6.0, succinate), 2.71 (t, 2H, J=6, succinate), 3.52-3.55 (m, 2H, NHCH$_2$), 4.22 (t, 2H, J=4.9, CH$_2$O), 6.00 (bs, 1H, NH). $^{13}$C NMR (CDCl$_3$): d 14.68, 22.81, 25.83, 29.31, 29.36, 29.42, 29.50, 29.65, 29.72, 29.75, 29.76, 32.10, 36.01, 38.15, 63.50, 172.78, 173.18, 174.12.

Mass (m/z) M$^+$=399.5.

Example 2

N-Palmitoylethanolamine-O-(succinyl(methoxypolyethylene glycol(1000))

Intermediate 1 (1.00 g, 2.63 mmol) was neutralized with an equivalent amount of tetrabuthylammonium hydroxide in methanol and the resulted salt solution was brought to dryness under vacuum. The dry salt was reacted with methoxypolyethylene glycol (1000) tosylate (3.95 mmol) in 40 ml of anhydrous tetrahydrofuran. The mixture was stirred at room temperature for 4 h. The mixture was evaporated and reconstituted in 15 ml of water. The crude product was purified by reverse-phase chromatography using water as eluent. Yield: 90%. Mass (m/z): M$^+$=1426. Water solubility: ≥10 mg/ml Example 3

N-Octadecanoylethanolamine-O-(phtaloyl(triethylene glycol))

1 g of N-Octadecanoylethanolamine (3.05 mmol) was dissolved in 50 ml anhydrous dioxane. 0.67 g of phtalic anhydride (4.5 mmol) was added and the mixture kept under stirring at 40° C. for 5 h. The intermediate phtaloyl ester was recovered by filtration and used without further purification. It was reacted with 0.593 g of triethyleneglycol (3.95 mmol) in the presence of 0.03 g dimethylaminopyridine (DMAP) (0.26 mmol) and 0.54 g dicyclohexylcarbodiimide (DCC) (2.63 mmol) in 40 ml of anhydrous dimethylformamide. The mixture was stirred at room temperature for 4 h. Then the formed precipitate was filtered off and the filtrate was evaporated and reconstituted in 15 ml of chloroform. A saturated solution of NaHCO$_3$ was added and the aqueous phase was then extracted twice with chloroform. Organic phases were collected, dried over anhydrous MgSO$_4$ and evaporated in vacuum. The crude product was purified by chromatography on a silica gel column using chloroform as eluent. 1HNMR (CDCl3): d 0.88 (t, 3H), 1.26-1.33 (m, 28H), 1.60-1.65 (m, 2H), 2.23 (t, 2H), 3.53-3.58 (dd, 2H), 3.77 (t, 2H), 3.60-3.69 (m, 6H), 4.25 (t, 2H), 4.36 (t, 2H), 7.60 (d, 2H), 7.74 (d, 2H)

Mass (m/z): M$^+$=618.1

Example 4

N-Palmitoylethanolamine-O-(phtaloyl(methoxypolyethylene glycol(1000))

1 g of Palmitoylethanolamide (3.3 mmol) was dissolved in 50 ml anhydrous dioxane. 0.67 g of phtalic anhydride (4.5 mmol) was added and the mixture kept under stirring at 40° C. for 5 hr. The intermediate phtaloyl ester was recovered by filtration and used without further purification. It was neutralized with equivalent amount of tetrabuthylammonium hydroxide in methanol and the resulted salt solution was brought to dryness under vacuum. The dry salt was reacted with methoxypolyethylene glycol (1000) tosylate (3.95 mmol) in 40 ml of anhydrous tetrahydrofuran. The mixture was stirred at room temperature for 4 h. The mixture was evaporated and reconstituted in 15 ml of water. The crude product was purified by reverse-phase chromatography using water as eluent. Yield: 86%. Mass (m/z): $M^+$=1474. Water solubility: ≥10 mg/ml.

Example 5

N-Oleoylethanolamine-O-(glutaryl(tetraethylene glycol))

1 g oleoylethanolamide (OEA) (3.07 mmol) was reacted with 0.53 g of glutaric anhydride (4.5 mmol) in 10 ml of dry dimethylformamide. The mixture was kept under stirring at room temperature for 1 h. Then 3 ml of HCl 2N and 20 ml of cold water were added and the mixture was extracted 3 times with 10 ml chloroform. Organic phases were collected, dried over anhydrous $MgSO_4$ and evaporated in vacuum. The crude product was purified by chromatography on a silica gel column using a mixture 9.8/0.2 chloroform/methanol as eluent. The product was finally crystallized from chloroform/hexane 1:1. $^1$HNMR ($CDCl_3$): d 0.88 (t, 3H), 1.27-1.33 (m, 8H), 1.35 (m, 2H), 1.63 (m, 2H), 1.92 (m, 2H), 2.01 (dd, 4H), 2.31 (t, 2H), 2.40-2.45 (m, 4H), 5.37 (m, 2H), 4.22 (t, 2H), 4.29 (t, 3H)

Mass (m/z): $M^+$=440.5 (425)

The intermediate glutaryl ester was reacted with 0.752 g of tetraethyleneglycol (3.95 mmol) in the presence of 0.03 g dimethylaminopyridine (DMAP) (0.26 mmol) and 0.54 g dicyclohexylcarbodiimide (DCC) (2.63 mmol) in 20 ml of anhydrous tetrahydrofuran. The mixture was stirred at room temperature for 4 h. Then the formed precipitate was filtered off and the filtrate was evaporated and reconstituted in 15 ml of chloroform. A saturated solution of $NaHCO_3$ was added and the aqueous phase was then extracted twice with chloroform. Organic phases were collected, dried over anhydrous $MgSO_4$ and evaporated in vacuum. The crude product was purified by chromatography on a silica gel column using 9.5/0.5 chloroform/methanol as eluent. Yield: 88%.

$^1$HNMR ($CDCl_3$): d 0.88 (t, 3H), 1.27-1.33 (m, 8H), 1.35 (m, 2H), 1.63 (m, 2H), 1.92 (m, 2H), 2.01 (dd, 4H), 2.31 (t, 2H), 2.40-2.45 (m, 4H), 3.53-3.58 (dd, 2H), 3.65-3.73 (m, 12H), 4.31 (t, 2H), 5.37 (m, 2H)

Mass (m/z): $M^+$=617.6

Example 6

N-[2-PEG400-0-carbonyl-oxy-ethyl]-octadecanamide 0.5 g di stearoylethanolamide (SEA) (1.5 mmol) and 0.26 g of 1,1'-carbonyldiimidazole (1.65 mmol), were reacted in 20 ml anhydrous chloroform. The mixture was kept under stirring at room temperature for 1.5 h. 0.82 g of di PEG 400 (2.25 mmol) were then added and the mixture heated at 60° C. for 12 h. The mixture was then cooled and extracted once with 10 ml 5% citric acid and then with 10 ml of 5% $NaHCO_3$. The organic layer was collected and dried under vacuum. The crude product was purified on a reverse phase column using a mixture acetonitrile/water 8:2 as eluent. Yield: 92%. Mass (m/z): $M^+$=756. Water solubility: >10 mg/ml.

Example 7

N-[2-methoxypolyethylene glycol(5000)-O-carbonyl-oxy-ethyl]-palmitamide 5.0 g of Methoxypolyethylene glycol (5000) dissolved in 50 ml anhydrous tetrahydrofuran at −15° C. was treated in a sealed equipment with phosgene gas obtained by the controlled decomposition of 150 mg of triphosgene at 100° C. with phenanthridine as catalyst. The solution was kept under stirring at −15° C. for 2 h and then exhaustively purged with nitrogen flow to remove acid and triphosgene excess which are decomposed by bubbling in an alkaline cool solution. The chlorocarbonate derivative was used without further purification. 0.3 g of palmitoyletanolamide and 0.15 g of triethylamine were added to the solution still kept under nitrogen at −15° C. The mixture was stirred for 1 h at −15° C. and then brought for 1 h at 0° C. The mixture was finally evaporated to dryness under vacuum. The crude product was purified by chromatography on a reverse phase column using water as eluent. Yield 90%. Mass (m/z): 5329. Water solubility: >10 mg/ml.

Example 8a

N-Palmitoylethanolamine-O-(succinyl(diethylene glycol))

1.00 g of intermediate 1 (2.63 mmol) was reacted with 0.42 g of diethyleneglycol (3.95 mmol) in the presence of 0.03 g dimethylaminopyridine (DMAP) (0.26 mmol) and 0.54 g dicyclohexylcarbodiimide (DCC) (2.63 mmol) in 40 ml of anhydrous tetrahydrofuran. The mixture was stirred at room temperature for 4 h. Then the formed precipitate was filtered off and the filtrate was evaporated and reconstituted in 15 ml of chloroform. A saturated solution of $NaHCO_3$ was added and the aqueous phase was then extracted twice with chloroform. Organic phases were collected, dried over anhydrous $MgSO_4$ and evaporated in vacuum. The crude product was purified by chromatography on a silica gel column using 9.5/0.5 chloroform/methanol as eluent. Yield: 75%. $^1$H NMR ($CDCl_3$): d 0.87 (t, 3H, J=6.9, $CH_3$), 1.26-1.31 (m, 26H, $CH_2$), 1.58-1.64 (m, 2H, $CH_2$), 2.17 (t, 2H, J=8.0, $CH_2CO$), 2.62-2.70 (m, 4H, succinate), 3.50-3.54 (m, 2H, $NHCH_2$), 3.61 (t, 2H, J=5.0, $CH_2$ f), 3.69-3.74 (m, 4H, $CH_2$ d-e), 4.20 (t, 2H, J=5.0, $CH_2O$), 4.27 (t, 2H, J=4.0, $CH_2$ a), 5.97 (bs, 1H, NH). $^{13}$C NMR ($CDCl_3$): d 14.70, 22.79, 25.85, 29.34, 29.40, 29.45, 29.51, 29.63, 29.71, 29.75, 29.76, 32.12, 36.04, 38.12, 61.00, 63.05, 63.51, 68.80, 72.47, 172.78, 173.25, 175.46. Mass (m/z): $M^+$=487.67

Example 8b

N-Palmitoylethanolamine-O-(succinyl(triethylene glycol))

1.00 g of intermediate 1 (2.63 mmol) was reacted with 0.593 g of triethyleneglycol (3.95 mmol) in the presence of 0.03 g dimethylaminopyridine (DMAP) (0.26 mmol) and 0.54 g dicyclohexylcarbodiimide (DCC) (2.63 mmol) in 40 ml of anhydrous tetrahydrofuran. The mixture was stirred at room temperature for 4 h. Then the formed precipitate was filtered off and the filtrate was evaporated and reconstituted in 15 ml of chloroform. A saturated solution of $NaHCO_3$ was added and the aqueous phase was then extracted twice with chloroform. Organic phases were collected, dried over anhydrous $MgSO_4$ and evaporated in vacuum. The crude product was purified by chromatography on a silica gel column using 9.5/0.5 chloroform/methanol as eluent. Yield: 73%. $^1$H NMR (CDCl$_3$): d 0.88 (t, 3H, J=6.9, CH$_3$), 1.27-1.32 (m, 26H, CH$_2$), 1.58-1.64 (m, 2H, CH$_2$), 2.18 (t, 2H, J=8.0, CH$_2$CO), 2.63-2.71 (m, 4H, succinate), 3.53-3.57 (m, 2H, NHCH$_2$), 3.61 (t, 2H, J=5.0, CH$_2$ f), 3.66-3.74 (m, 8H, b-e), 4.21 (t, 2H, J=5.0, CH$_2$O), 4.28 (t, 2H, J=5.0, CH$_2$ a), 5.99 (bs, 1H, NH)$^{13}$C NMR (CDCl$_3$): d 14.65, 22.80, 25.83, 29.35, 29.41, 29.46, 29.54, 29.65, 29.73, 29.76, 29.78, 32.13, 36.10, 38.14, 61.05, 63.05, 63.54, 68.85, 70.24, 72.47, 172.78, 173.25, 175.46. Mass (m/z): M$^+$=531.72

Example 8c

N-Palmitoylethanolamine-O-(succinyl(tetraethylene glycol))

1.00 g of intermediate 1 (2.63 mmol) was reacted with 0.752 g of tetraethyleneglycol (3.95 mmol) in the presence of 0.03 g dimethylaminopyridine (DMAP) (0.26 mmol) and 0.54 g dicyclohexylcarbodiimide (DCC) (2.63 mmol) in 40 ml of anhydrous tetrahydrofuran. The mixture was stirred at room temperature for 4 h. Then the formed precipitate was filtered off and the filtrate was evaporated and reconstituted in 15 ml of chloroform. A saturated solution of NaHCO$_3$ was added and the aqueous phase was then extracted twice with chloroform. Organic phases were collected, dried over anhydrous MgSO$_4$ and evaporated in vacuum. The crude product was purified by chromatography on a silica gel column using 9.5/0.5 chloroform/methanol as eluent. Yield: 70%. $^1$H NMR CDCl$_3$: d 0.88 (t, 3H, J=7.0, CH$_2$), 1.26-1.31 (m, 26H, CH$_2$), 1.58-1.64 (m, 2H, CH$_2$), 2.18 (t, 2H, J=8.0, CH$_2$CO), 2.62-2.70 (m, 4H, succinate), 3.53-3.57 (m, 2H, NHCH$_2$), 3.63 (t, 2H, J=5.0, CH$_2$ f), 3.65-3.75 (m, 12H, b-e), 4.22 (t, 2H, J=5.0, CH$_2$O), 4.25 (t, 2H, J=5.0, CH$_2$ a), 6.0 (bs, 1H, NH). $^{13}$C NMR CDCl$_3$: d 14.67, 22.80, 25.85, 29.34, 29.41, 29.47, 29.55, 29.67, 29.72, 29.75, 29.79, 32.15, 36.11, 38.15, 61.10, 63.07, 63.54, 68.85, 70.24, 70.46, 72.47, 172.79, 173.27, 175.47. Mass (m/z): M$^+$=576.4

Biological Part

Skin accumulation was evaluated in vivo by topical application of PEA and its derivatives on the dorsal surface of mice. Recovery of tissues and lipid extraction was followed by HPLC quantitative determination, using pre-column derivatization with dansyl chloride, as described in B. Yagen, S. Burnstein: *Novel and sensitive method for the detection of anandamide by the use of its dansyl derivative.* J Chromatog B 740:93-9 (2000). PEA and its derivatives were then tested for their anti-inflammatory and anti-hyperalgesic effects, using the carrageenan induced oedema model and the mechanical hyperalgesia model in order to understand whether PEG moieties were able to improve skin accumulation and prolong the pharmacological effects of the parent molecule.

In Vivo Experiments

Animals

Male Swiss mice weighing 25 to 30 g were purchased from Harlan (Udine, Italy). They were housed in stainless steel cages in a room kept at 22±1° C. on a 12/12-h light/dark cycle. The animals were acclimated to their environment for 1 week, and they had ad libitum access to tap water and standard rodent chow.

Protocol

PEA (10 mg/5 ml) and its derivatives (Derivative Example no 8a, Derivative Example 8b, Derivative Example 8c, at equimolecular doses) were dissolved in absolute ethanol. Each group of mice (n=6) was applied with 0.05 ml of ethanol solutions on dorsal surface of the left paw. After 5 minutes the animal received 50 µl of 1% λ-carrageenan in sterile saline injected into the treated paw. Absolute ethanol was used as vehicle in control animals. Paw oedema and mechanical hyperalgesia were evaluated at 2-4-6-8-24-48-72-96 h following λ-carrageenan injection.

Paw Oedema

Paw oedema development was measured by a plethysmometer (Ugo Basile, Milan, Italy). The increase in paw volume was evaluated as the difference between the paw volume measured at each time point and the basal paw volume measured at time 0 (before drug application and carrageenan injection).

Mechanical Hyperalgesia

Mechanical hyperalgesia was assessed by measuring of latency (s) to withdraw the paw from a constant mechanical pressure exerted onto its dorsal surface. A 15-g calibrated glass cylindrical rod (diameter=10 mm) chamfered to a conical point (diameter=3 mm) was used to exert the mechanical force. The weight was suspended vertically between two rings attached to a stand and was free to move vertically. A cut off time of 90 sec. was used.

Ex Vivo Experiments

Lipid Extraction

In a separate set of experiments, the animals received local application of PEA or its derivatives (Derivative Example no 8a, Derivative Example 8b, Derivative Example 8c) on the paw; following 2-4-6-24-48-72-96 h, mice were killed and paws were excised. Frozen tissues samples were weighed and homogenized in a solution of methanol and a serine protease inhibitor, phenylmethylsulphonyl fluoride (PMSF, 1 mM). Then, homogenate tissues were subjected to methanol-chloroform-water (1:2:1, v/v/v) extraction. After centrifugation, the organic layer was carefully removed, transferred to another vial and purified by silica gel (60-Å, 230-400 mesh) micro-columns.

Skin Accumulation

Molecules of interest were isolated by small-scale chromatography. Glass microcolumns (5 cm, ø 50 mm) were used. 1 ml of a mixture (1/1 v/v) of chloroform and silica gel (0.04-0.063 mm, 230-400 mesh, Macherey-Nagel) was used to load the columns. Samples were dissolved in 1 ml of chloroform and then loaded. Columns were washed with 1 ml of chloroform and 2 ml of chloroform/methanol (9/1 v/v), thus obtaining the fractions of interest that were collected and evaporated in vacuum. The extraction method was validated in blank experiments by treating skin with a known amount of each analyzed compound. Recovery percentages were calculated as well and they resulted higher than 85% for all the tested products.

HPLC Analysis

HPLC analysis was performed on a Jasco apparatus (Jasco inc., Easton, Md., USA) composed by a quaternary gradient pump (PU 2089 Plus), a 25 µl Rheodyne injection valve and a multi-wave length UV detector (MD 2010 Plus). The analytical method used was described by B. Yagen, S. Burnstein: Novel and sensitive method for the detection of anandamide by the use of its dansyl derivative. J Chromatog B 740:93-9 (2000). It was assessed according to USP 30 for the analysis of PEA and its derivatives. The specificity (absence of interfering peak from skin samples) was assessed as well.

Statistical Analyses

Results are expressed as mean±S.E.M. of n experiments. All analyses were conducted using Graph-Pad Prism (GraphPad Software Inc., San Diego, Calif.). The significance of differences between groups was determined by Student t-test (for ex vivo experiments) and two-way analysis of variance (ANOVA) followed by Bonferroni post hoc tests for multiple comparisons (for in vivo experiments). Difference with P<0.05 (*) was considered statistically significant.

Results

Effects of Epidermal Application of PEA and Derivatives on Carrageenan-Induced Hyperalgesia and Paw Oedema As expected, carrageenan injection into the mice paw produced both significant hyperalgesia (FIG. 1a white bars) and paw oedema (FIG. 1b white circles). Topically applied PEA (1 mg/paw) markedly reduced mechanical hyperalgesia and paw oedema in a time dependent manner, as shown by the increase in paw withdrawal latency (FIG. 1a black bars) and results in reduction of paw volume (FIG. 1b black triangles). In particular, anti-hyperalgesic and anti-inflammatory effects of PEA are significant at 2 and 4 h following application, whereas no effect was detectable at 6-96 h after topical application. The PEA-derivative 8a (1.6 mg/paw—i.e., equimolar dose of 1 mg PEA), showed a significant anti-hyperalgesic (FIG. 1a grey bars) and anti-inflammatory (FIG. 1b white squares) activities starting at h and lasting up to 72 h after local application. No effect was observed at earlier times (2-4 h).

The PEA derivative 8b (1.72 mg/paw—i.e., equimolar dose of 1 mg PEA) showed a significant anti-hyperalgesic (FIG. 2a grey bars) and anti-inflammatory (FIG. 2b white squares) activities, after 2 days of local application. These effects were significant up to 4 days following application of both derivatives (i.e., 8a and 8b).

Taking into consideration the results obtained by a single derivative application, we investigated the possible addictive effect of the drugs under study.

We found that the combination of PEA, derivative 8a and derivative 8b at equimolar doses (1; 1.6; 1.72 mg respectively) resulted in a rapid and long lasting anti-hyperalgesic (FIG. 3a black bars) and anti-inflammatory activities (FIG. 3b black triangles) as reported in FIG. 3.

Skin Accumulation

Results obtained from in vivo experiments were in accordance with data collected from skin accumulation experiments.

Extent of accumulation for topically applied PEA is reported in FIG. 4, compared to endogenous PEA. Data are expressed as nmol of PEA recovered per mg of skin. A high and statistically relevant amount of PEA is recovered from the skin, at 2 to 6 h after topical application. After 24 h, PEA levels return to baseline.

Results obtained after topical application of the derivative 8a are shown in FIG. 5 and are expressed as cumulative amount of derivative and PEA.

It is worthy of note that, during the whole period of analysis, the total amount accumulated in the skin (i.e. PEA+derivative) is almost 10 times higher than PEA alone. Similar results were obtained for derivatives 8b and 8c, as shown in FIG. 6.

The main difference among the tested derivatives seems to be the kinetic release of PEA, that is the biologically active molecule.

Derivative 8a has a faster release, starting from the $2^{nd}$ hour and sustained up to 72 hours.

Derivative 8b has a slower but prolonged release, since a relevant amount of PEA is detectable only at the 24 hours but is maintained up to 96 hours.

Since the biological activity belongs to PEA only, a comparison of the total amounts of PEA accumulated in the skin after PEA or derivative application has been performed. Results are shown in FIG. 7.

As shown above, the compounds of formula (I) result to possess an ideal hydrophilic/lipophilic balance, resulting in improved accumulation in the skin and a prolonged release of PEA.

Our results indicate derivatives 8a and 8b to accumulate in the skin and release PEA, in a time dependent manner. While the action of PEA has a rapid onset due to its rapid internalization and metabolism (2-4 h), its derivatives release PEA in a time and moiety depending manner, resulting in a significant prolongation of pharmacological effects. The release of PEA from derivatives is considered to depend upon the esterase activity, widely present in skin. We have also reported that compounds of formula (I) show the same pharmacological effects of the parent molecule in terms of efficacy, as confirmed by the increased levels of PEA in the skin after their application, as well as the reduction of carrageenan-induced hyperalgesia and paw oedema.

When polyethylene glycol esters of PEA are used, PEA levels in the skin are higher with respect to the parent drug (PEA) alone and a significant increase of detectable amounts of PEA is observed for several hours. It has also been found that mixing PEA with one or more compounds of formula (I), preferably in equimolar doses, results in an important, fast and long lasting antihyperlagesic and anti-inflammatory effect (2-96 h).

In view of the above, pharmaceutical formulations containing one or more derivatives of formula (I), together with pharmaceutically acceptable excipients and/or carriers are provided.

Preferably, the said pharmaceutical formulations are for topical application. In this case, in the compounds of formula (I), the number n will be preferably comprised between 1 and 10.

The said topical formulation can be a cream, an ointment, a gel, a suspension or a solution for spray delivery, a liniment, a patch and the like. The said formulation can contain various excipients and or carriers suitable to the kind of administration that is selected, according to what is known to the skilled person and reported for example in Remington's Pharmaceutical Sciences Handbook, Mack Pub. Co., N.Y., USA, 17th edition, 1985. For instance, the inventive formulation can contain: antioxidants such as ascorbic acid, propyl gallate, tocoferyl acetate; moisturizing agents such as gel of aloe barbadensis, glycereth-26, glycerin, sodium pyroglutamate; UV filters such as 3-benzophenon or PABA; preservatives such as methylparaben or dmdm idantoin, emollients such as organic esters, di- and triglycerids; antirritants such as NSAIDs, glycirrizates, etc.; synthetic or natural antibacterial such as triclosan, piroctone olamine, usnic acid, echinacea extracts undecylenic acid; natural or artificial fragrancies.

In other embodiments, the pharmaceutical formulations of the invention will be for oral or parenteral use. In this case, preferably, the number n in the compounds of formula (I) will be comprised between 11 and 1000.

For the oral administration, the pharmaceutical compositions may, for example, be in form of tablets or capsules prepared conventionally using pharmaceutically acceptable excipients such as bonding agents (for example pregelatinised maize starch, polyvinylpyrrolidone or hydroxypropyl methylcellulose); filler agents (for example lactose, microcrystalline cellulose or calcium hydrogen phosphate); lubricants (for example magnesium stearate, talc or silica);

disintegration agents (for example potato starch or sodium glycolate starch); or inhibiting agents (for example sodium lauryl sulfate). The tablets may be coated using the methods well known in the art. The liquid preparations for the oral administration may, for example, be in form of solutions, syrups or suspensions or they may be in form of lyophilized or granulated products to be reconstituted, before use, using water or other suitable carriers. Such oral liquid preparations may be prepared through conventional methods using pharmaceutically acceptable additives such as suspension agents (for example sorbitol syrups, cellulose or edible hydrogenated fats derivatives); emulsifying agents (for example lecithin or acacia); non-aqueous carriers (for example almond oil, oil-based esters, ethylic alcohol or fractionated vegetable oils); and preservatives (for example methyl- or propyl-p-hydroxybenzoates or sorbic acid). The preparation may also suitably contain flavours, colouring agents and sweetening agents.

The preparations for oral administration may be suitably formulated to allow the controlled release of the active ingredient.

For the buccal administration, the compositions may be in form of tablets, pills or granules formulated conventionally, suitable for absorption at the buccal-mucosa level. Typical buccal formulations are tablets for sublingual administration.

The compounds according to the present invention may be formulated for a parenteral administration by injection. The formulations for the injections may be in form of a single dosage for example in phials, with preservative added. The compositions may be in such form as suspensions, solutions or emulsions in oil-based or aqueous carriers and they may contain formulary agents such as suspension, stabilisation and/or dispersion agents. Alternatively, the active ingredient may be in form of powder to be reconstituted, before use, using a suitable carrier, for example using sterile water.

According to the present invention, the compounds may also be formulated according to rectal compositions such as suppositories or retention enema, for example containing the basic components of the common suppositories such as cocoa butter or other glycerides.

In addition to the previously described compositions, the compounds may also be formulated as depot preparations. Such long action formulations may be administered by implantation (for example through subcutaneous, transcutaneous or intramuscular implantation) or by intramuscular injection. Thus, for example, the compounds, according to the present invention may be formulated using suitable polymeric or hydrophobic materials (for example in form of an emulsion in a suitable oil) or ion-exchange resins or as minimally soluble derivatives, for example as a minimally soluble salt.

According to the present invention the dosing of the compounds of formula (I) proposed for the administration to a man (with body weight of about 70 kg) ranges from 0.1 mg to 1 g and preferably from 1 mg to 600 mg of the active principle per dose unit. The exact dosing will be at the discretion of the clinician.

According to the present invention, the dosing of the compounds of formula (I) to the pet patient (e.g., dogs and cats) will not exceed 14 mg/kg b.w., the exact dosing mainly depending on the kind and severity of the disease.

According to an embodiment, one or more compounds of formula (I) are administered together with a therapeutically active amount of palmitoylethanolamide or analogous acylethanolamides. A further object of the invention is therefore a compound of formula (I) for use in combination with a therapeutically active amount of palmitoylethanolamide or analogous acylethanolamides, in the treatment of inflammatory and itch- or pain-associated disorders, with separate, combined or sequential administration.

PHARMACEUTICAL PREPARATION EXAMPLES

Example 1

Cream for Application on Scarred Skin 100 g contain:

| | |
|---|---|
| N-Palmitoylethanolamine-O-(succinyl(triethylene glycol)) | g 2.50 |
| Vitamin E acetate | g 2.00 |
| Sodium hyaluronate | g 0.02 |
| Bronopol | g 0.05 |
| Sodium dehydroacetate | g 0.10 |
| Hydrogenated Castor oil | g 1.50 |
| Noveon AA1 | g 1.60 |
| Water to | g 100.00 |

Example 2

Cream for Application on Healthy Skin 100 g contain:

| | |
|---|---|
| N-Palmitoylethanolamine-O-(succinyl(triethylene glycol)) | g 3.50 |
| PEG-5 plant sterols | g 4.50 |
| Stearic Acid | g 3.00 |
| Cetostearylic alcohol | g 3.00 |
| Adelmidrol | g 0.50 |
| Glyceryl monostearate | g 1.50 |
| Carbopol 940 | g 0.40 |
| 2,4-dichlorobenzylic alcohol | g 0.15 |
| Bronopol | g 0.05 |
| Water to | g 100.00 |

Example 3

Fluid Cream for Application on Broad Skin Areas 100 g contain:

| | |
|---|---|
| N-Octadecanoylethanolamine-O-(phtaloyl(triethylene glycol)) | g 1.00 |
| Glycerol | g 5.00 |
| White mineral oil | g 3.00 |
| Silicone oil | g 1.00 |
| Glyceryl monostearate | g 1.40 |
| Cetostearylic alcohol | g 2.80 |
| Stearic acid | g 2.40 |
| PEG plant sterols | g 5.00 |
| Carbomer | g 0.10 |
| Bronopol | g 0.05 |
| Water to | g 100.00 |

Example 4

Gel for Oral Use 100 g contain:

| | |
|---|---|
| N-Octadecanoylethanolamine-O-(phtaloyl(triethylene glycol)) | g 3.20 |
| Glycerol | g 10.00 |
| Echinacea purpurea glyc. Extract | g 10.00 |
| Sodium alginate | g 2.50 |
| Sodium Hyaluronate | g 0.02 |
| Triclosan | g 0.025 |
| Bronopol | g 0.005 |
| Water to | g 100.00 |

Example 5

Lotion for Trichological Use 100 g contain:

| | |
|---|---|
| N-[2-PEG400-O-carbonyl-oxy-etil]-octadecanamide | g 1.50 |
| Adelmidrol | g 0.20 |
| D-biotine | g 0.04 |
| Echinacea pupurea glyc. Extract | g 10.00 |
| Ethyl alcohol | g 40.00 |
| Water to | g 100.00 |

Example 6

Vaginal Gel 100 g contain:

| | |
|---|---|
| N-Palmitoylethanolamine-O-(phtaloyl(methoxypolyethylene glicol(1000)) | g 2.50 |
| Glycerol | g 10.00 |
| Vitamin A palmitate | g 0.20 |
| 2-phenylethanol | g 0.15 |
| Hydrogenated Castor oil 40(OE) | g 1.00 |
| Methyl para-oxybenzoate | g 0.05 |
| Noveon AA1 | g 1.00 |
| Sodium Hyaluronate | g 0.04 |
| Water to | g 100.00 |

Example 7

Gel for Balano-Preputial Use 100 g contain:

| | |
|---|---|
| N-Palmitoylethanolamine-O-(phtaloyl(methoxypolyethylene glicol(1000)) | g 0.25 |
| Glycerol | g 10.00 |
| Vitamin A palmitate | g 0.20 |
| 2-phenylethanol | g 0.18 |
| Bronopol | g 0.05 |
| Noveon AA1 | g 0.80 |
| Sodium Hyaluronate | g 0.04 |
| Water to | g 100.00 |

Example 8

Drops for Otological Use 100 g contain:

| | |
|---|---|
| N-[2-Methoxypolyethylene glicol(5000)-O-carbonyl-oxyethyl]-palmitamide | g 4.00 |
| Transcutol P | g 49.00 |
| Propylene glycol | g 30.00 |
| Deo-Usnate | g 0.30 |
| Triclosan | g 0.20 |
| Phytosfingosin | g 0.15 |
| Trans-traumatic acid | g 0.06 |
| Water to | g 100.00 |

Example 9

Gel for Rectal Microclysma 100 g contain:

| | |
|---|---|
| N-Palmitoylethanolamine-O(phtaloyl(methoxypolyethylene glycol(1000)) | g 0.25 |
| Glycerol | g 8.00 |
| Trans-traumatic acid | g 0.50 |
| 2-phenylethanol | g 0.10 |
| Hydrogenated Castor oil 40(OE) | g 1.00 |
| Methyl-paraoxybenzoate | g 0.05 |
| Noveon AA1 | g 0.50 |
| Water to | g 100.00 |

Example 10

Patch for Prolonged Dermal Application 100 cm$^2$ contain:

| | |
|---|---|
| N-Palmitoylethanolamine-O-(succinyl(triethylene glycol)) | mg 40.00 |
| Trans-traumatic acid | mg 2.00 |
| Adelmidrol | mg 10.00 |
| Gluing vehicle to | mg 80.00 |

Example 11

Gel for Periungual Use 100 g contain:

| | |
|---|---|
| N-Oleoylethanolamine-O-(glutaryl(tetraethylene glycol)) | g 2.50 |
| Trans-traumatic acid | g 0.10 |
| Sodium alginate | g 2.50 |
| Eumulgin L | g 1.00 |
| Undecylenic acid | g 0.25 |
| Bronopol | g 0.10 |
| Hyaluronic acid | g 0.10 |
| Water to | g 100.00 |

Example 12

Sterile Eyewash for Corneal Use 100 g contain:

| | |
|---|---|
| N-[2-Methoxypolyethylene glycol(5000)-O-carbonyl-oxy-ethyl]-palmitamide | g 0.30 |
| Trans-traumatic acid | g 0.05 |
| Phosphate buffer 0.1M to | g 2.50 |

Example 13

Eye Drop

Each 5 ml eye drop bottle, contains:

| | |
|---|---|
| N-Palmitoylethanolamine-O-(phtaloyl(methoxypolyethylene glycol(1000)) | mg 10.00 |
| Palmitoilethanolamide | mg 1.25 |
| methyl-beta-cyclodextrin | mg 50.00 |
| Hyaluronic acid sodium salt | mg 5.00 |
| Na2HPO4 | mg 4.00 |
| NaH2PO4 | mg 1.12 |
| NaCl | mg 35.00 |
| Bi-distilled water q.s. to | ml 5.00 |

Example 14

Mouthwash for Oral Use 100 g contain:

| | |
|---|---|
| N-[2-Methoxypolyethylene glycol(5000)-O-carbonyl-oxy-ethyl]-palmitamide | g 2.00 |
| Adelmidrol | g 0.50 |
| Trans-traumatic acid | g 0.05 |
| Glycerol | g 7.00 |
| Sodium Pyroglutamate | g 3.00 |
| Hydrogenated Castor oil 40 (OE) | g 2.00 |
| Noveon AA1 | g 0.50 |
| Hyaluronic acid sodium salt | g 0.05 |
| 2,4-dichlorobenzylic alcohol | g 0.15 |
| Bronopol | g 0.10 |
| Water to | g 100.00 |

Example 15

Tablets for Oral Use

Each tablet contains:

| | |
|---|---|
| N-Palmitoylethanolamine-O-(succinyl(methoxypolyethylene glycol(1000)) | mg 600.00 |
| Palmitoilethanolamide ultramicronized | mg 150.00 |
| Mycrocrystalline cellulose | mg 78.47 |
| Crosscaramellose sodium | mg 45.00 |
| Polyvinylpyrrolidone | mg 10.00 |
| Magnesium stearate | mg 4.00 |
| Polisorbate 80 | mg 2.00 |

Example 16

Tablets for Oral Use

Each tablet contains:

| | |
|---|---|
| N-Palmitoylethanolamine-O-(succinyl(methoxypolyethylene glycol(1000)) | mg 1200.00 |
| Palmitoilethanolamide ultramicronized | mg 300.00 |
| Mycrocrystalline cellulose | mg 155.00 |
| Crosscaramellose sodium | mg 90.00 |
| Polyvinylpyrrolidone | mg 20.00 |
| Magnesium stearate | mg 8.00 |
| Polisorbate 80 | mg 4.00 |

Example 17

Tablets for Oral Use

Each tablet contains:

| | |
|---|---|
| N-Palmitoylethanolamine-O-(phtaloyl(methoxypolyethylene glycol(1000)) | mg 800.00 |
| Palmitoilethanolamide ultramicronized | mg 200.00 |
| Trans-Polidatin | mg 40.00 |
| Pharmacologically acceptable excipients | mg 225.00 |

Example 18

Tablets for Oral Use

Each tablet contains:

| | |
|---|---|
| N-Palmitoylethanolamine-O-(phtaloyl(methoxypolyethylene glycol(1000)) | mg 1200.00 |
| Palmitoylethanolamide ultramicronized | mg 400.00 |
| Pharmacologically acceptable excipients | mg 326.00 |
| Luteolin | mg 80.00 |

Example 19

Sticks of Dispersible Powder

Each stick contains:

| | |
|---|---|
| N-Palmitoylethanolamine-O-(phtaloyl(methoxypolyethylene glicol(1000)) | mg 1200.00 |
| Diacerein | mg 300.00 |
| Pharmaceutically acceptable excipients | mg 2500.00 |

Example 21

Microgranules for Sublingual Use

Each dose contains:

| | |
|---|---|
| N-Palmitoylethanolamine-O-(succinyl(methoxypolyethylene glycol(1000)) | mg 1200.00 |
| Palmitoylethanolamide ultramicronized | mg 300.00 |
| Powder sorbitol | mg 384.00 |

17
-continued

| | |
|---|---|
| Sucrose palmitate | mg 13.00 |
| Polysorbate 80 | mg 3.00 |

Example 21

Bottles with Cap-Container for Oral Use

A 5 ml dose of sterile suspension, for pediatric use, in a bottle with pierceable cap-container, contains:
in the pierceable cap-container:

| | |
|---|---|
| N-Palmitoylethanolamine-O-(phtaloyl (methoxypolyethylene glycol(1000)) | mg 250.00 |
| Palmitoylethanolamide ultramicronized | mg 50.00 |
| Lactose | mg 50.00 |
| in the bottle: | |
| Carboxymethylcellulose | mg 25.00 |
| Bi-distilled water q.s. to | ml 5.00 |

Example 22

Liophilized Phials

Each 4 ml lyophilized phial contains:

| | |
|---|---|
| N-Palmitoylethanolamine-O-(succinyl (methoxypolyethylene glycol(1000)) | mg 200.00 |
| Mannitol | mg 80.00 |
| Polyvinylpyrrolidone | mg 20.00 |
| Each 3 ml solvent phial contains: | mg 4.00 |
| Na2HPO4 | |
| NaH2PO4 | mg 1.12 |
| Bi-distilled water q.s. to | ml 3.00 |

Example 23

Soft Gelatin Oil-Based Capsules for Veterinary Use (Dog and Cat)

Each capsule contains:

| | |
|---|---|
| N-Palmitoylethanolamine-O-(succinyl(methoxypolyethylene glycol(1000)) | mg 400.00 |
| Phosphatidylserine | mg 50.00 |
| Resveratrol | mg 60.00 |
| Oil based excipients | mg 300.00 |

Example 24

Suppositories for Rectal Use

Each suppository contains:

| | |
|---|---|
| N-[2-PEG400-O-carbonyl-oxy-ethyl]-octadecanamide | mg 250.00 |
| N-Palmitoylethanolamine-O-(succinyl(triethyleneglycol)) | mg 150.00 |
| Saturated fatty acids triglycerides | mg 1000.00 |

Example 25

Bottles for Intravesical Instillation

Each 50 ml bottle contains:

| | |
|---|---|
| N-[2-Methoxypolyethylene glycol(5000)-O-carbonyl-oxy-ethyl]-palmitamide | mg 3600.00 |
| Adelmidrol | mg 1000.00 |
| Hyaluronic acid | mg 500.00 |
| Sterile bi-distilled water q.s. to | ml 50.00 |

Example 26

Bottles for Intravenous Administration

Each 500 ml sterile bottle contains:

| | |
|---|---|
| N-Palmitoylethanolamine-O-(phtaloyl(methoxypolyethylene glycol(1000)) | mg 2000.00 |
| Soy lipids | g 50.00 |
| Egg Phospholipids | g 6.00 |
| Sterile bi-distilled water q.s. to | ml 500.0 |

The diseases that can be treated by the compounds of the invention are skin diseases, particularly of inflammatory origin.

Preferred diseases to be treated are selected from: inflammatory diseases, of allergic or autoimmune nature, of the skin, eye or mucous membranes; disorders of wound healing; ear disorders (e.g., otitis externa), the vulvodynias and the vestibulodynias; the vulvar vestibulitis; the inflammatory reactions of the mucous and mucocutaneous tissues of the oral cavity and the dental pulp; the dermo-epidermal neuralgias of the small fibres, nociceptive and/or pruriceptive, with neuropathic basis as the postherpetic neuralgia; the diabetes-associated neuralgias; the neuralgia due to HIV infection; the neuropathic and/or psicogenic itches; the granulomas affecting the dermoepidermal tissue; the dermatologic diseases, also with immunological genesis, characterized by neuroinflammatory processes, both acute and chronic.

The invention claimed is:

1. A polyethylene glycol derivative of acylethanolamide of formula (I):

$$R-CONHCH_2CH_2O-A-O-(CH_2CH_2O)_n-CH_2CH_2OR' \quad (I)$$

wherein R—CONHCH$_2$CH$_2$O— is the residue of acylethanolamide, wherein R is selected from: a linear or branched alkyl chain including from 9 to 21 carbon atoms; or a linear or branched alkenyl chain including from 9 to 21 carbon atoms and one double bond;
R' is H or a linear or branched alkyl group chosen among methyl-, ethyl-, n-propyl- and isopropyl-;
A is a linker group selected from a dicarboxylic acid residue or a carbonyl group —CO—;
and n is an integer from 1 to 10.

2. Formula (1) according to claim 1, wherein n is an integer from 1 to 3.

3. Formula (1) according to claim 1, wherein, when A is a dicarboxylic acid residue, A is selected from a succinic, glutaric, maleic or phthalic acid residue.

4. A pharmaceutical formulation containing one or more compounds of formula (I) as defined in claim 1, together with pharmaceutically acceptable excipients and/or carriers.

5. The pharmaceutical formulation of claim 4, comprising a therapeutically effective amount of the compounds of formula (I).

6. The pharmaceutical formulation of claim 4, wherein the pharmaceutical formulation is formulated for topical use.

7. The pharmaceutical formulation of claim 6, wherein the formulation is selected from a cream, an ointment, a gel, a suspension or a solution for spray delivery, an eyewash, a liniment and a patch.

8. The pharmaceutical formulation of claim 4, wherein the pharmaceutical formulation is formulated as an oral or parenteral formulation.

* * * * *